(12) United States Patent
Eckman

(10) Patent No.: US 7,871,441 B2
(45) Date of Patent: Jan. 18, 2011

(54) CERVICAL FIXATION DEVICE

(75) Inventor: Walter W. Eckman, Tupelo, MS (US)

(73) Assignee: Concept Matrix, LLC, Orlando, FL (US)

( * ) Notice: Subject to any disclaimer, the term of this patent is extended or adjusted under 35 U.S.C. 154(b) by 526 days.

(21) Appl. No.: 11/741,200

(22) Filed: Apr. 27, 2007

(65) Prior Publication Data

US 2008/0015581 A1    Jan. 17, 2008

Related U.S. Application Data

(60) Provisional application No. 60/745,895, filed on Apr. 28, 2006.

(51) Int. Cl.
*A61F 2/44* (2006.01)
(52) U.S. Cl. .............. 623/17.11; 623/17.12; 623/17.13; 623/17.14; 623/17.15; 623/17.16
(58) Field of Classification Search .................. 606/279; 623/17.11
See application file for complete search history.

(56) References Cited

U.S. PATENT DOCUMENTS

| 4,349,921 | A | 9/1982 | Kuntz |
|---|---|---|---|
| 4,545,374 | A | 10/1985 | Jacobson |
| 4,936,848 | A | 6/1990 | Bagby |
| 4,961,740 | A | 10/1990 | Ray et al. |
| 5,258,031 | A | 11/1993 | Salib et al. |
| 5,425,773 | A | 6/1995 | Boyd et al. |
| 5,522,899 | A | 6/1996 | Michelson |
| 5,549,679 | A | 8/1996 | Kuslich |
| 5,562,738 | A | 10/1996 | Boyd et al. |
| 5,571,189 | A | 11/1996 | Kuslich |
| D377,095 | S | 12/1996 | Michelson |
| D377,096 | S | 12/1996 | Michelson |
| D377,527 | S | 1/1997 | Michelson |
| 5,593,409 | A | 1/1997 | Michelson |
| 5,607,424 | A * | 3/1997 | Tropiano .................. 623/17.16 |
| 5,609,636 | A | 3/1997 | Kohrs et al. |

(Continued)

FOREIGN PATENT DOCUMENTS

EP    1112753 B1    7/2001

(Continued)

OTHER PUBLICATIONS

Scient'x Catalogue, www.scientx.com, 2006.

(Continued)

*Primary Examiner*—Thomas C Barrett
*Assistant Examiner*—Sameh Boles
(74) *Attorney, Agent, or Firm*—Panitch Schwarze Belisario & Nadel LLP

(57) ABSTRACT

A cervical fixation device, for insertion between a pair of adjacent cervical vertebrae, includes a frame comprised of a first material. The frame has a generally rectangular proximal end and a generally rectangular distal end. The distal end is connected to the proximal end by at least one upper arch and at least one lower arch. The upper and lower arches are spaced apart from each other. The frame has a generally hollow interior, substantially open lateral sides between the upper and lower arches and a substantially open proximal end.

12 Claims, 9 Drawing Sheets

U.S. PATENT DOCUMENTS

| | | | |
|---|---|---|---|
| 5,645,596 | A | 7/1997 | Kim et al. |
| 5,653,761 | A | 8/1997 | Pisharodi |
| 5,669,909 | A | 9/1997 | Zdeblick et al. |
| 5,674,296 | A | 10/1997 | Bryan et al. |
| 5,702,449 | A | 12/1997 | McKay |
| 5,776,199 | A | 7/1998 | Michelson |
| 5,785,710 | A | 7/1998 | Michelson |
| 5,888,226 | A | 3/1999 | Rogozinski |
| 5,980,522 | A | 11/1999 | Koros et al. |
| 5,984,967 | A | 11/1999 | Zdeblick et al. |
| 6,039,762 | A | 3/2000 | McKay |
| D425,989 | S | 5/2000 | Michelson |
| 6,102,950 | A | 8/2000 | Vaccaro |
| 6,113,637 | A | 9/2000 | Gill et al. |
| 6,126,688 | A | 10/2000 | McDonnell |
| 6,136,031 | A | 10/2000 | Middleton |
| 6,174,334 | B1 | 1/2001 | Suddaby |
| 6,193,757 | B1 * | 2/2001 | Foley et al. ............... 623/17.16 |
| 6,231,610 | B1 | 5/2001 | Geisler |
| 6,235,059 | B1 | 5/2001 | Benezech et al. |
| 6,245,108 | B1 | 6/2001 | Biscup |
| 6,270,528 | B1 | 8/2001 | McKay |
| 6,309,421 | B1 | 10/2001 | Pisharodi |
| 6,419,705 | B1 | 7/2002 | Erickson |
| 6,425,920 | B1 | 7/2002 | Hamada |
| 6,447,547 | B1 | 9/2002 | Michelson |
| 6,454,805 | B1 | 9/2002 | Baccelli et al. |
| 6,468,311 | B2 | 10/2002 | Boyd et al. |
| 6,478,823 | B1 | 11/2002 | Michelson |
| 6,520,991 | B2 | 2/2003 | Huene |
| 6,527,803 | B1 | 3/2003 | Crozet et al. |
| 6,558,424 | B2 * | 5/2003 | Thalgott ................... 623/17.16 |
| 6,582,433 | B2 | 6/2003 | Yun |
| 6,648,917 | B2 | 11/2003 | Gerbec et al. |
| 6,852,129 | B2 * | 2/2005 | Gerbec et al. ............. 623/17.15 |
| 6,855,168 | B2 | 2/2005 | Crozet |
| 7,044,972 | B2 * | 5/2006 | Mathys et al. ............ 623/17.16 |
| 7,137,997 | B2 * | 11/2006 | Paul ......................... 623/17.11 |
| 7,503,933 | B2 * | 3/2009 | Michelson ................ 623/17.11 |
| 2001/0018614 | A1 | 8/2001 | Bianchi |
| 2002/0116009 | A1 | 8/2002 | Fraser et al. |
| 2003/0004576 | A1 | 1/2003 | Thalgott |
| 2004/0054412 | A1 | 3/2004 | Gerbec et al. |
| 2004/0199251 | A1 | 10/2004 | McCombe et al. |
| 2004/0254644 | A1 | 12/2004 | Taylor |
| 2005/0004672 | A1 * | 1/2005 | Pafford et al. ............. 623/17.11 |
| 2005/0010290 | A1 | 1/2005 | Hawkins |
| 2005/0131539 | A1 * | 6/2005 | Kohrs ....................... 623/17.11 |
| 2006/0206208 | A1 | 9/2006 | Michelson |
| 2007/0038545 | A1 | 2/2007 | Smith et al. |
| 2007/0233247 | A1 * | 10/2007 | Schwab ..................... 623/17.11 |

FOREIGN PATENT DOCUMENTS

| | | |
|---|---|---|
| FR | 2794967 A1 | 12/2000 |
| RU | 1424826 | 9/1988 |
| WO | 9640014 A1 | 12/1996 |
| WO | 9714377 A1 | 4/1997 |
| WO | 97/37620 | 10/1997 |
| WO | 9932054 A1 | 7/1999 |
| WO | 02/080818 | 10/2002 |
| WO | WO2007038545 | 4/2007 |

OTHER PUBLICATIONS

Depraetere, P., et al., Interbody Cages in PLIF Surgery: A Multicentric Report, Journal of Musculoskeletal Research, vol. 2, No. 1 (1998) 9-14.

Helmut D. Link et al., "Link SC Charité Artificial Disc: History, Design & Biomechanics", Spinal Restabilization Procedures. Edited by D.L. Kaech and J.R. Jinkins, 297-298 (2002), Berlin, Germany.

Paul C. Mcafee, "Artificial Disc Prothesis: The Link SB Charité III™", Spinal Restabilization Procedures, edited by D.L. Kaech and J.R. Jinkin, 299-301 (2002) Towson, MD.

"Spine Arthroplasty", Spine Industry Analysis Series, Viscogliosi Bros., LLC, Nov. 2001.

Ofice Action, dated May 29, 2009, in related U.S. Appl. No. 11/741,446.

Benezech, J., et al., The PCB, success of the year!, Scient'x News Letter, No. 3, Jan. 2003. 2 pages.

Benezech, J., The origins of the PCB, Scient'x News Letter, No. 6, Apr. 2003, 2 pages.

Search Report, issued Jul. 16, 2009, in related European Patent Appln. No. 09005645.8.

Search Report, issued Sep. 12, 2009, in related European Patent Appln. No. 07008690.5.

Search Report, dated Jul 16, 2009, in related European Application No. 09005645.8.

Search Report, dated Sep. 12, 2007, in related European Application No. 07008690.5.

Office Action, dated May 29, 2009, in related U.S. Appl. No. 11/741,446.

Office Action, dated Nov. 27, 2009, in related U.S. Appl. No. 11/741,446.

Benezech, J., Integrated Cervical Plate-Cage, 1 pages (Admitted Prior Art).

Benezech, J., et al., The PCB, success of the year!, Scient'x News Letter, No. 3, Jan. 2003, 2 pages.

Benezech, J., The origins of the PCB, Scient'x News Letter, No. 6, Apr. 2003, 2 pages.

Helmut D. Link et al., "Link SB Charité Artificial Disc: History, Design & Biomechanics", Spinal Restabilization Procedures. Edited by D.L. Kaech and J.R. Jinkins, 297-298 (2002), Berlin, Germany.

Paul C. Mcafee, "Artificial Disc Prosthesis: The Link SB Charité III™", Spinal Restabilization Procedures, edited by D.L. Kaech and J.R. Jinkins, 299-301 (2002) Towson, MD.

"Link SB Charité™ Artificial Disc" Brochure, Maintaining Natural Mobility, Link Spine Group, Branford, Connecticut.

"Prodisc" Brochure, Spine Solutions: The Non-Fusion Technology Company.

"Spine Arthroplasty", Spine Industry Analysis Series, Viscogliosi Bros., LLC, Nov. 2001.

* cited by examiner

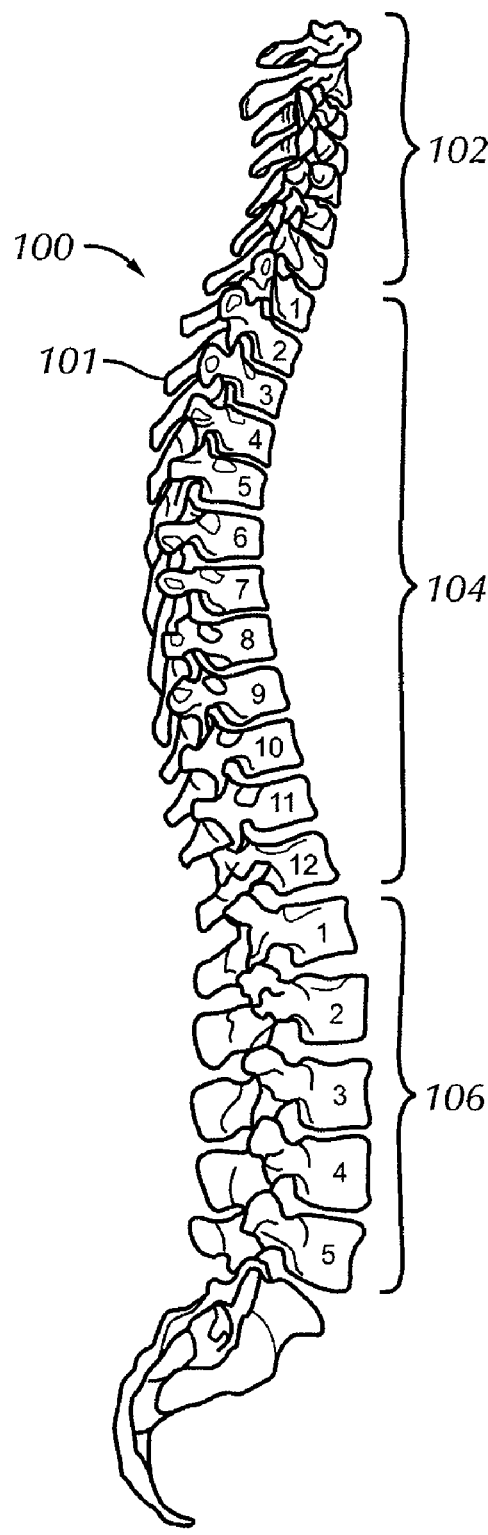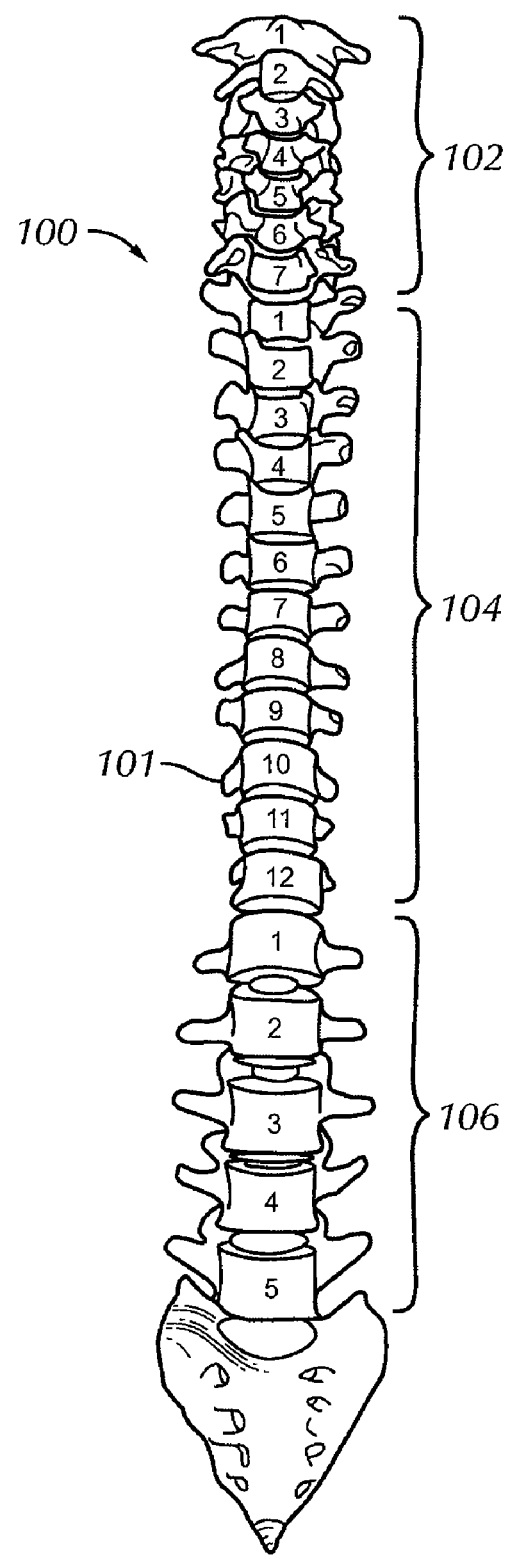
FIG. 7A
*(Prior Art)*
FIG. 7B
*(Prior Art)*

US 7,871,441 B2

CERVICAL FIXATION DEVICE

CROSS-REFERENCE TO RELATED APPLICATIONS

This application claims the benefit of U.S. Provisional Patent Application No. 60/745,895 filed Apr. 28, 2006 entitled "Dual Composition Vertebral Defect Device" which is incorporated by reference herein in its entirety.

BACKGROUND OF THE INVENTION

The present invention relates generally to vertebral fixation or defect devices, and more particularly to cervical fixation devices for insertion into an intervertebral space.

As shown in prior art FIGS. 7A-11, it is known in the prior art that the spine 100, also known as the spinal column or vertebral column, supports the upper body, allows head, neck, and trunk motion, and includes twenty-four moveable vertebrae 101 including seven cervical vertebrae 102, twelve thoracic vertebrae 104, and five lumbar vertebrae 106, which extend from the skull to the sacrum.

Referring to FIG. 8, with the exception of the first, upper most cervical vertebra 102, each vertebra 101 has a vertebral body 108, a lamina 110, a spinous process 112, as well as facet structures 114 (which form facet joints), two transverse processes 116, and two pedicles 118, one on each side. Each individual vertebra 101 has a large foramen 120, which forms the spinal canal (not shown) when the vertebrae 101 are in their normal anatomical position forming the spine 100. The spinal cord and major nerve fiber groups pass through and are protected by the spinal canal. A strong fibrous membrane, the dura mater (not shown), also known as the dura, surrounds the spinal cord, nerve fibers, and fluid in the spinal canal.

Referring now to FIGS. 8 and 9, each pair of adjacent vertebrae 101 along with interconnecting soft tissues and an intervertebral disk 128 constitutes a motion segment 122, also known as a functional spinal unit, and the combined motions of many of such motion segments constitute overall spinal motion at any one time. The joining of two vertebrae 101 also creates two neuroforaminae 124, also known as intervertebral foraminae, one on each side, each of which is bordered by a facet joint 126 dorsally, a pedicle 118 superiorly, a pedicle 118 inferiorly, and an intervertebral disk 128 ventrally. Each neuroforamina 124 allows passage of large nerve roots (not shown) and associated blood vessels (not shown). The intervertebral disk 128 resides in the space between adjacent vertebral bodies, the intervertebral space 130, also known as the interbody space or disk space. The level of each particular intervertebral space 130 and intervertebral disk 128 is identified by naming the vertebrae 101 superior and inferior to it, for example L 4-5 in the case of the intervertebral space 130 and intervertebral disk 128 between the fourth and fifth lumbar vertebrae 106.

Referring to FIG. 10, each intervertebral disk 128 includes a collection of peripheral concentric rings comprised of strong ligaments known as annular ligaments 132, also known as the annulus, and a softer central area of normally well hydrated material known as the nucleus 134. The annular ligaments 132 are arranged at different angles in alternate layers such that they provide support and stability, resisting excessive vertebral body 108 rotation and axial motion when proper tension is maintained. Although described by some as a cushion, the nucleus 134 is relatively incompressible in a young healthy spine, and thus its major role is to provide support and tension of the annular ligaments 132 to maintain stability while allowing a limited range of motion.

Referring now to FIG. 11, with the exception of the first cervical vertebra (not shown), in a cervical vertebra 102 the inferior surface of the vertebral body 108 is concave (as shown in phantom), while the superior surfaces are flatter centrally and curl laterally to form the uncinate processes, which partially articulate with the inferior surface of the vertebral body of the adjacent superior vertebra. Owing to the shapes of the inferior and superior surfaces of the vertebral bodies 108, the cervical intervertebral space 130 and intervertebral disk 128 are convex on the superior side but flatter on the inferior side. Cervical intervertebral disks are generally flatter and thinner than lumbar and thoracic intervertebral disks.

Situations arise in which one or more cervical vertebrae 102 do not have adequate support or stability, which can lead to pain, deformity, stenosis of spinal canal or neuroforamina, and impairment or loss of nerve function. In some cases, surgical spine fusion is considered. Spine fusion is a process of growing bone between two or more adjacent vertebrae 101 such that the adjacent vertebrae 101 will move only in unison. This process involves placing bone, or material to guide or stimulate bone growth, in proximity to exposed bone of the vertebrae 101, and then allowing time for new bone to grow and form a structurally strong connection, or fusion, between the vertebrae 101. The earliest such procedures took place approximately a century ago, and the procedures have developed over many years, including various attempts to fuse posterior structures of the spine such as the spinous process 112, lamina 110, facet joint 114, and transverse processes 116.

Recently, there has been more interest in fusion involving bone growth directly between adjacent vertebral bodies 108. Large amounts of well vascularized bone are in close proximity, there is a large surface area available, and the inherent compression force applied between vertebral bodies by muscle tension and the upright position of the human body enhances bone formation and strength. The intervertebral disk space 130 has therefore become a major focus in interbody fusion surgery. The intervertebral disk space 130 is cleaned as much as possible, and cartilage and abnormal surface bone, also known as endplate bone, from adjacent vertebral bodies 108 is removed, after which material is placed in the space to promote fusion. However, loose bone fragments do not provide structural support and therefore fusion is often unsuccessful. Structural bone grafts from the patient or donors have been successful, but may give rise to pain and complications if from the patient, and risk of disease transmission if from a donor.

Vertebral defect devices are increasingly used to assist with fusion between vertebral bodies 108. Such devices are intended to provide support to prevent excessive collapse of space between vertebrae 101 which could result in stenosis of the spinal canal or neuroforamina, progressive deformity, impairment or loss of nerve function, or pain. Such devices also provide at least one compartment to fill with bone, or material which assists in bone growth, in order to maintain close contact with vertebral bone as new bone is encouraged to bridge across the space involved.

Referring to FIG. 6, which shows a single plan view of a vertebra 101, it is known in the art that interbody devices can be inserted from several directions (indicated by arrowed lines) including posterior interlaminar approaches on both sides A, B, transforaminal or partially lateral approaches C, D, anterior approaches E, and straight lateral approaches F.

Though vertebral defect devices have proven useful in the lumbar or thoracic spine 104, 106, posterior and transforaminal placement (A, B, C, D) of any device is too dangerous in the cervical spine 102. Some cylindrical bone grafts and devices have also been associated with increased subsidence and kyphotic deformities, particularly in the cervical area. Subsidence is the sinking of devices or structural bone grafts into adjacent vertebral bodies.

Interbody devices have been constructed with polymers such as PEEK and carbon fiber/PEEK combinations. These devices have the advantage of minimal interference with future imaging studies whether by x-ray, CT scan, or MRI scan. Such devices usually have simple implanted metal markers in front and back to allow limited visualization of their position with x-rays or the like. Such devices are made with thick, vertically straight walls to provide support strength, but once they subside a small amount the straight walls offer no effective resistance to excessive subsidence. The surface area provided for fusion is also limited by the thick walls. Polymer material in current use does not allow construction of sharp edges and fixation elements and does not allow for varied shapes which might solve many of the problems with subsidence.

In the cervical spine 102, it is known in the art that the addition of an anterior plate will limit subsidence and kyphotic deformity, but this adds cost and is not always successful. Complications such as backing out of fixation screws and screw and plate breakage have been significant problems. Anterior plates are difficult to install if more than two disk levels are fused, and may add to dysphagia. In addition, such a plate occupies much of the anterior surface of the superior and inferior vertebral bodies, and there is data to suggest that proximity of the plate to the adjacent disks promotes more rapid degenerative changes. If surgery is required at an adjacent level, it is almost always necessary to remove the plate to perform the surgery, which increases complexity and morbidity when further surgery is required.

It is therefore desirable to provide a cervical fixation device designed to achieve rapid fixation while preventing excessive subsidence. The device should eliminate the need for ancillary stabilization devices such as anterior cervical plates and should be completely or nearly completely contained within the confines of the disk space. The device should have excellent support strength, but limit the amount of interference with future imaging studies.

BRIEF SUMMARY OF THE INVENTION

Briefly stated, the present invention is directed to a cervical fixation device for insertion between a pair of adjacent cervical vertebrae. The cervical fixation device includes a frame comprised of a first material. The frame has a generally rectangular proximal end and a generally rectangular distal end. The distal end is connected to the proximal end by at least one upper arch and at least one lower arch. The upper and lower arches are spaced apart from each other. The frame has a generally hollow interior, substantially open lateral sides between the upper and lower arches and a substantially open proximal end.

In another aspect, the invention is directed to a method of installing a cervical fixation device. The method includes the steps of: making an incision in an anterior region of a patient proximate a small gap between a first cervical vertebra and a second cervical vertebra of a spine of the patient, inserting a distal end of a surgical instrument and removing disk material from an intervertebral space between the first and second vertebrae, preparing the first and second vertebrae for fusion, inserting the cervical fixation device with protective covers into the intervertebral disk space such that the proximal end of the cervical fixation device is generally flush with an anterior edge of the first and second vertebrae, and removing the protective covers to expose an interior of the cervical fixation device and the at least one projection extending from the cervical fixation device.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 7A is a right side elevation view of a human spinal column as is known in the art;

FIG. 7B is a front elevation view of a human spinal column as is known in the art;

DETAILED DESCRIPTION OF THE INVENTION

Figure 1A:
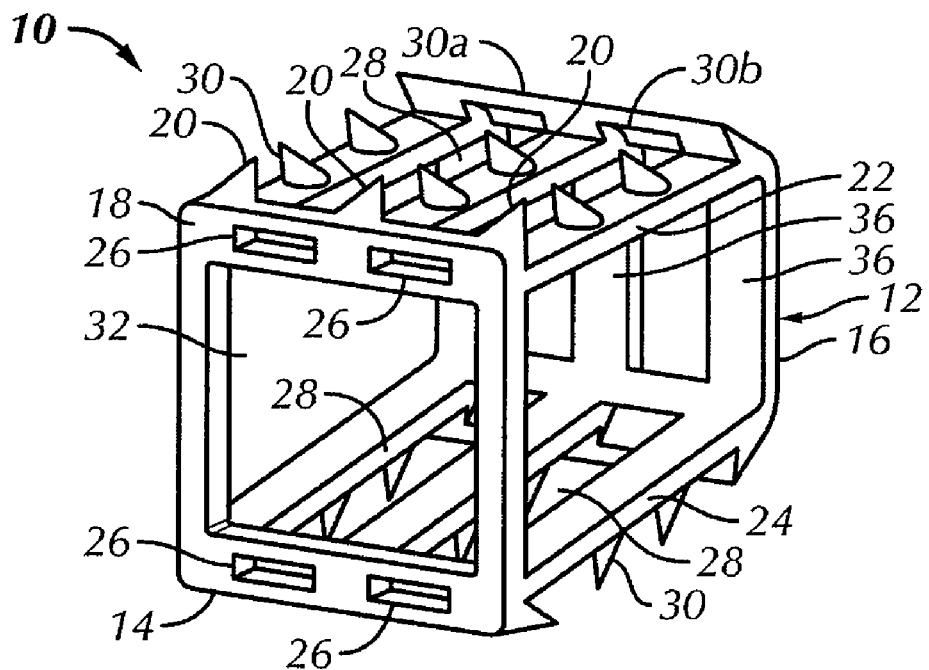
FIG. 1A is right side rear perspective view of a first preferred embodiment of a cervical fixation device in accordance with the present invention.
Figure 1B:
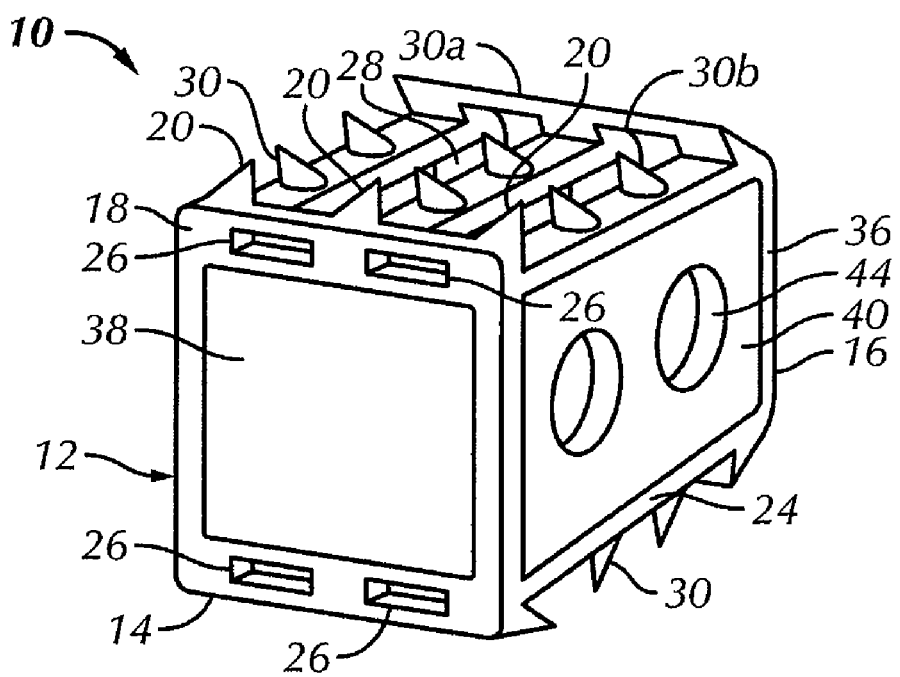
FIG. 1B is a right side rear perspective view of the cervical fixation device of FIG. 1A including an insert.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of a cervical fixation device in accordance with the present invention, and designated parts thereof. The terminology includes the words noted above, derivatives thereof and words of similar import. Unless specifically set forth herein, the terms "a", "an" and "the" are not limited to one element but instead should be read as meaning "at least one".

Referring to the drawings in detail, wherein like reference numerals indicate like elements throughout, there is shown in FIGS. 1A-5B a cervical fixation device, generally designated 10, 210, in accordance with first and second preferred embodiments of the present invention for insertion between a pair of adjacent cervical vertebrae 102. Unless specifically set forth herein, the description and method of the first preferred embodiment 10 also applies to the second preferred embodiment 210.

Referring now to FIGS. 1A-4, the cervical fixation device includes a frame 12 comprised of a first material. The frame 12 is preferably formed from a machining process, and the least amount of the first material to provide adequate compressive strength and mechanical stability is used. The first material is preferably a surgical grade titanium and is discernable by electromagnetic imaging, such as x-rays and computed tomography (CT) scans, but has minimal interference with magnetic resonance imaging (MRI) scans. The first material may be selected from the group consisting of a generally rigid biocompatible material such as machined bone graft, titanium, a nickel plated metal, a biocompatible alloy, a biocompatible ceramic, a biocompatible polymeric material or a biologically absorbable material. Though the above materials are preferred, any material allowing adequate support strength that could be machined, milled or otherwise formed into the shapes and features disclosed below and that would have minimal interference with imaging studies could be used without departing from the spirit and scope of the invention.

Figure 6:
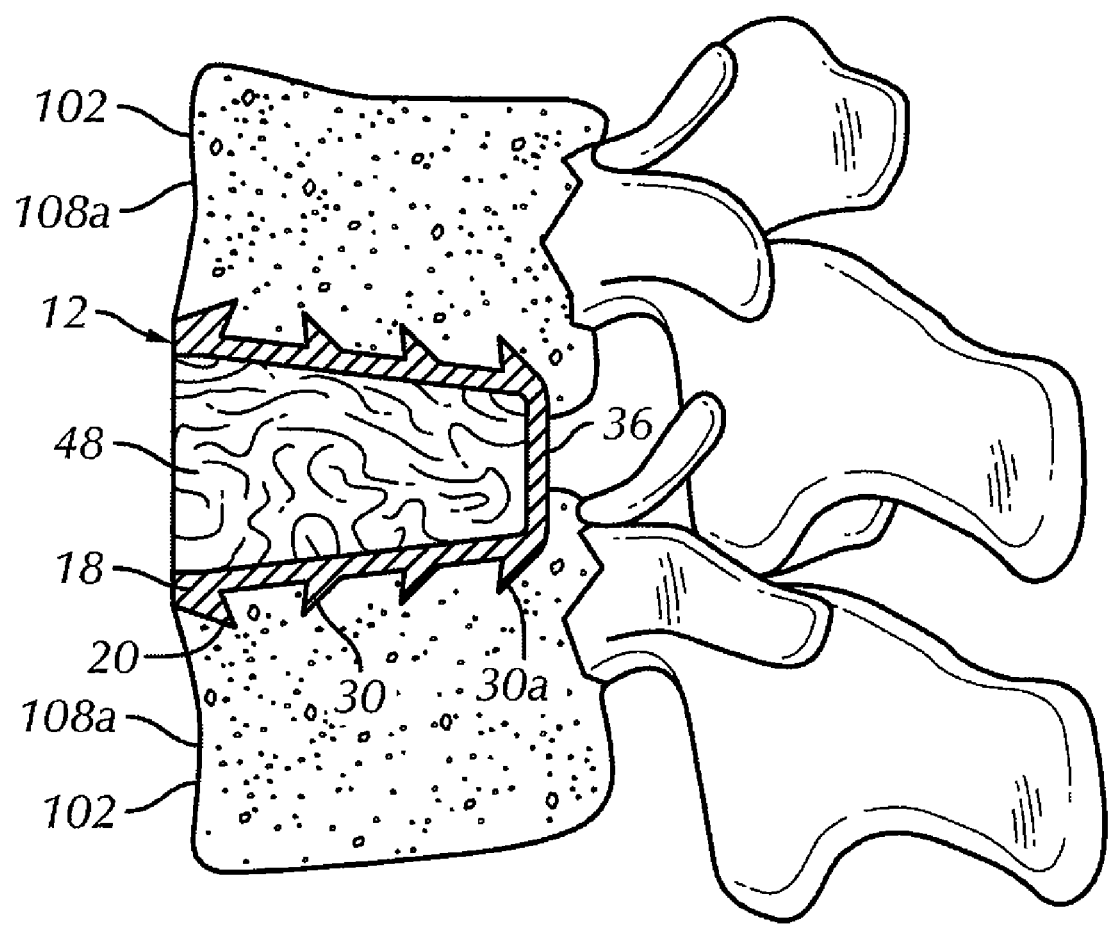
FIG. 6 is a left side cross sectional view of the cervical fixation device of FIG. 1A inserted into a vertebral disk space.
Figure 8:
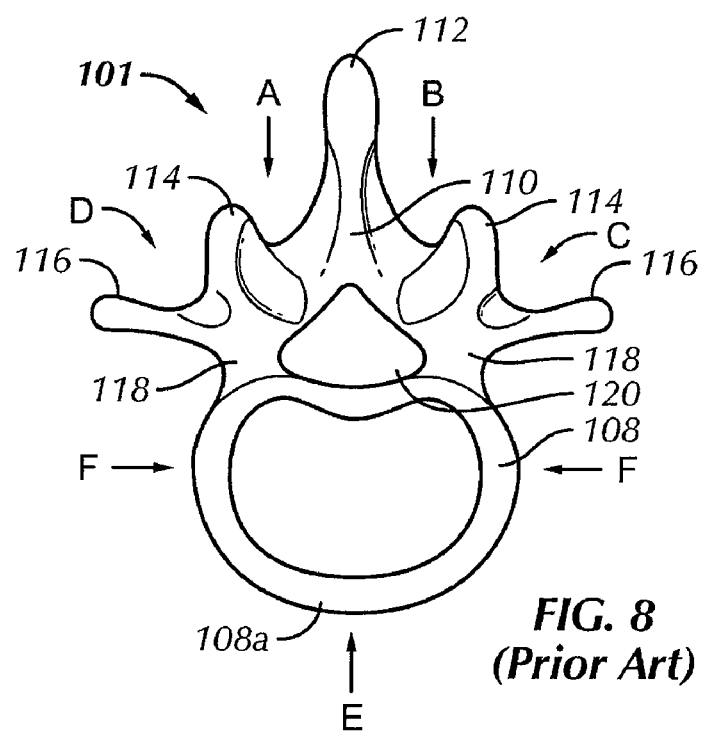
FIG. 8 is a top plan view of a human vertebra as is known in the art.
Figure 9:
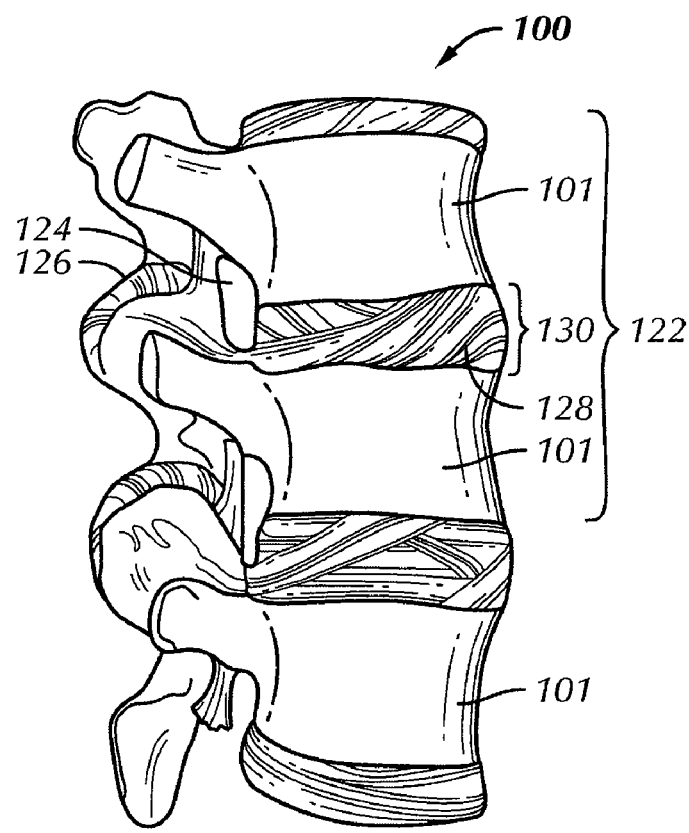
FIG. 9 is a right side elevation view of a portion of the lumbar spine as is known in the art.
Figure 10:
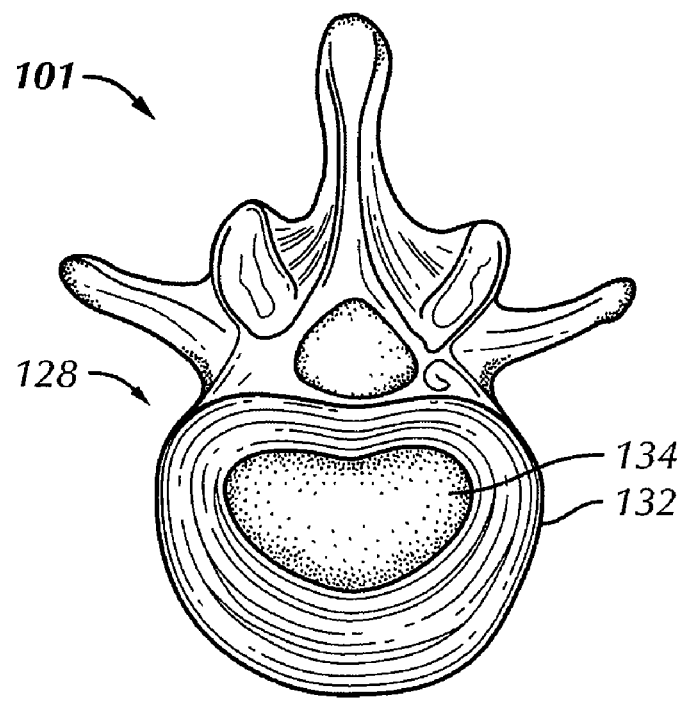
FIG. 10 is a top plan view of a lumbar vertebra as is known in the art.
Figure 11:
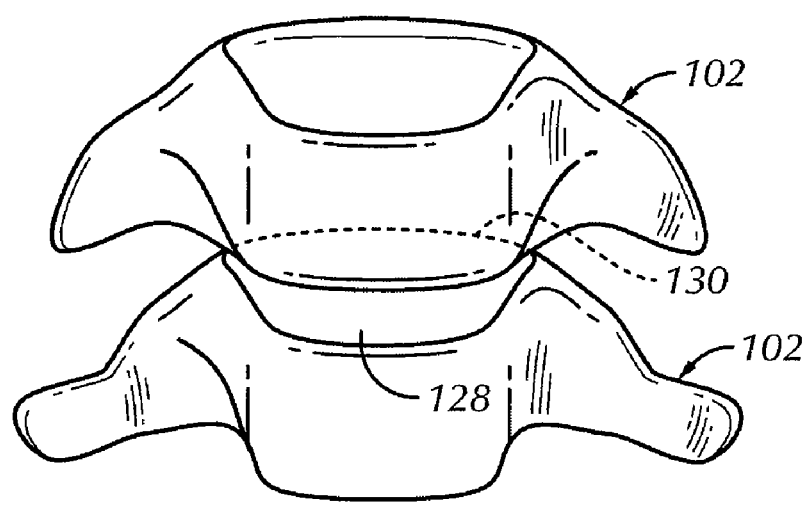
FIG. 11 is a front view of a pair of cervical vertebrae as is known in the art.

The frame 12 includes a generally rectangular proximal end 14 and a generally rectangular distal end 16. A longitudinal axis of the frame 12 extends from the proximal end 14 to the distal end 16. The proximal end 14 and distal end 16 may be rounded to form more of an oval or circular shape. The proximal end 14 preferably includes flanges 18 vertically extending above and below the remainder of the frame 12. The flanges 18 preferably extend a minimal amount past the proximal end 14 in the vertical direction and preferably not in the lateral direction. Because the flanges 18 do not extend laterally outwardly more than a maximum width of the cervical fixation device 10, the lateral field of view is not obstructed during insertion of the cervical fixation device 10. The flanges 18 act as a stopper to prevent excessive distal placement or migration of the cervical fixation device 10, to help eliminate the risk of spinal canal encroachment and to aid in fixation. The flanges 18 abut the anterior edge of the cervical vertebrae 102 being fused together when the cervical fixation device 10 is installed as shown in FIG. 6. The flanges 18 may each include at least one projection 20. The projections 20 preferably point toward the distal end 16 of the cervical fixation device 10 in order to engage with the vertebrae 102 above and below the cervical fixation device 10. The projections 20 may be comprised of a plurality of distally pointing conical spikes as shown or may be an elongated edge extending at least partially along the flange 18. For example, the outer periphery of the flange 18 may be sharpened, curved or pointed to form the projections 20.

The flanges 18 and the proximal end 14 may be partially curved laterally with the convexity toward the proximal end 14 to match or better fit the contour or curve of the anterior leading edges of the adjacent vertebrae 102 once the vertebrae 102 are prepared for fixation. When the cervical fixation device 10 is fully inserted (see FIG. 6), the flanges 18 are preferably flush, or nearly flush, with the anterior edges of the vertebrae 102 above and below the cervical fixation device 10 so that there is minimal, if any, of the cervical fixation device 10 protruding anterior to the adjacent vertebrae.

The distal end 16 of the cervical fixation device 10 is connected to the proximal end 14 by at least one upper arch 22 and at least one lower arch 24. Preferably, the at least one upper arch 22 is permanently attached to the at least one lower arch 24 by the proximal and distal ends 14, 16 and both arches 22, 24 extend from the proximal end 14 to the distal end 16. Preferably, the cervical fixation device 10 includes three upper arches 22 and three lower arches 24 that are generally parallel and spaced apart. Between or proximate each arch 22, 24 is a gap 28 configured to allow bone growth into the intervertebral space 130. Four slots 26 preferably extend through the flanges 18, two spaced apart slots 26 for each flange 18. The slots 26 are generally aligned with the gaps 28. Though three arches 22, 24 and two gaps 28 are shown and described, it is within the spirit and scope of the invention that a single arch or planar segment with apertures of any geometry, or additional arches and gaps be used to connect the proximal and distal ends 14, 16.

Each of the arches 22, 24 preferably includes at least one and preferably two partially sharpened projections 30. The projections 30 are preferably conically shaped and extend outwardly from the arches 22, 24 and slant toward the proximal end 14. The projections 30 are preferably disposed at equally spaced intervals along each of the respective arches 22, 24. The top and bottom of the distal end of the cervical fixation device 10 also preferably each include a sharpened edge 30a. The sharpened edge 30a is preferably a laterally extending edge that also slants toward the proximal end 14. The sharpened edges 30a extend both from the top and bottom of the distal end 16. The sharpened edges 30a may include receiving slots 30b which are aligned with the gaps 28. The sharpened edges 30a, with or without receiving slots 30b, provide a smooth fit and transition to covers 46 (described below). The sharpened edge 30a along with inserted covers 46, allow for smooth insertion of the cervical fixation device 10.

The projections 30 and sharpened edge 30a each act as a barb and assist with securely retaining the cervical fixation device 10 in place between a pair of vertebrae 102. Once the cervical fixation device 10 is inserted in place and the covers 46 are removed, the proximal slant of the projections 30 and sharpened edges 30a penetrate into the bone of the adjacent vertebrae 102 to resist extrusion of the cervical fixation device 10 and provide rapid fixation and stabilization of the adjacent vertebrae 102 to promote fusion. Though conical projections 30 are preferred, the projections 30 may have any shape such as an elongated triangle or edge and may or may not be included on each arch 22, 24. Any number of projections 30 may be made in any number of shapes, and in any number of arrangements, so long as the requisite retaining and fixation function is achieved, without departing from the spirit and scope of the invention.

The frame 12 has a generally hollow interior 32 and substantially open lateral sides between the upper and lower arches 22, 24. The proximal end 14 is also substantially open. The generally hollow interior 32 forms an open interior chamber that is generally defined by the shape of the frame 12. The interior 32 may house bone grafts or non-bone matter to aid in fusion of the adjacent vertebrae 102. FIG. 6 shows the inserted cervical fixation device 10 with bone 48 after healing.

Figure 2A:
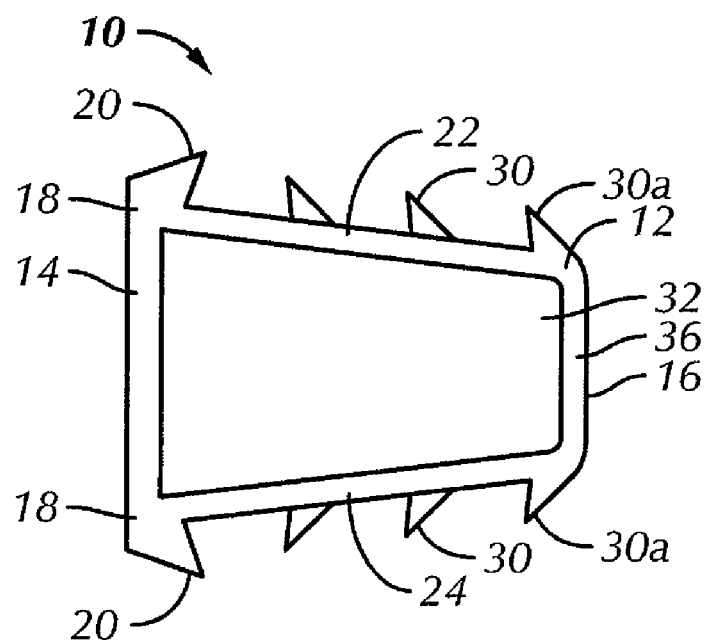
FIG. 2A is a right side elevation view of the cervical fixation device shown in FIG. 1A.
Figure 2B:
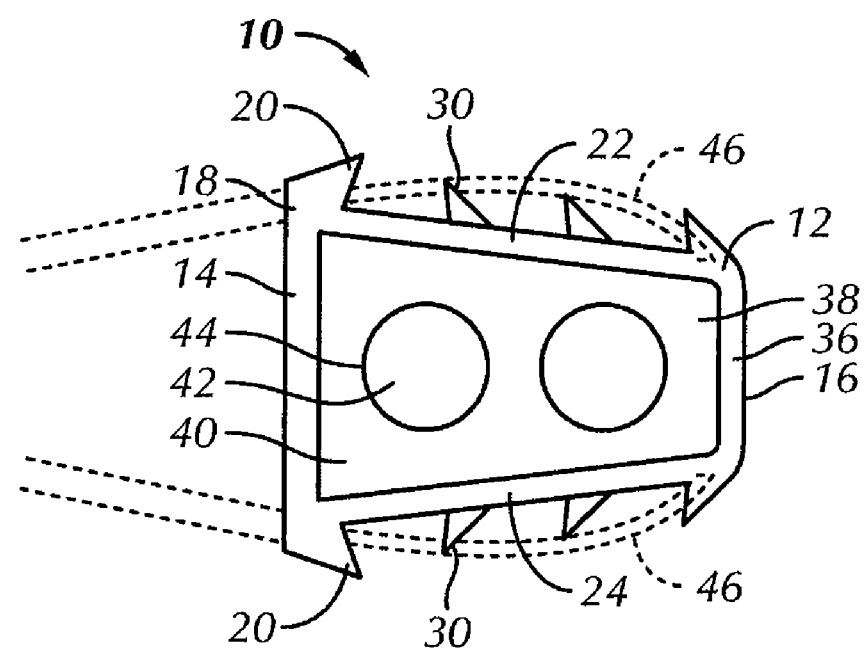
FIG. 2B is a right side elevation view of the cervical fixation device shown in FIG. 1B.
Figure 3A:
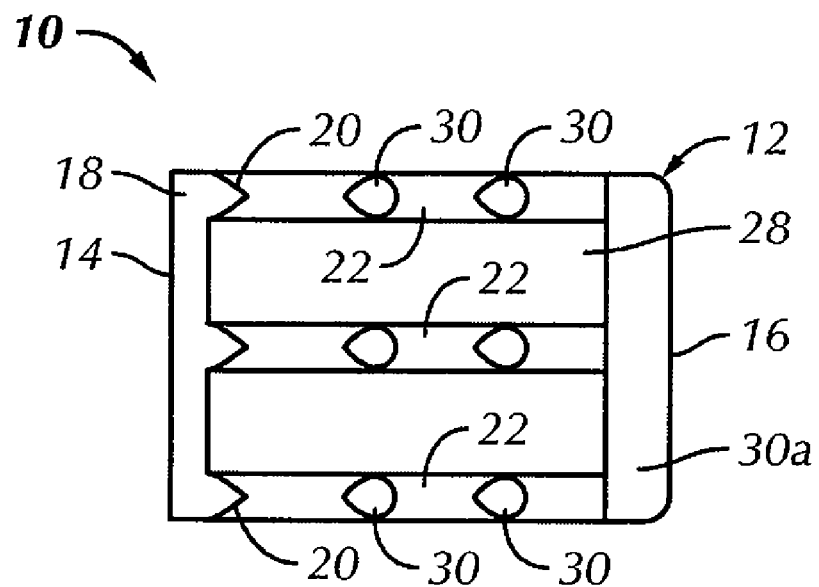
FIG. 3A is a top plan view of the cervical fixation device shown in FIG. 1A.
Figure 3B:
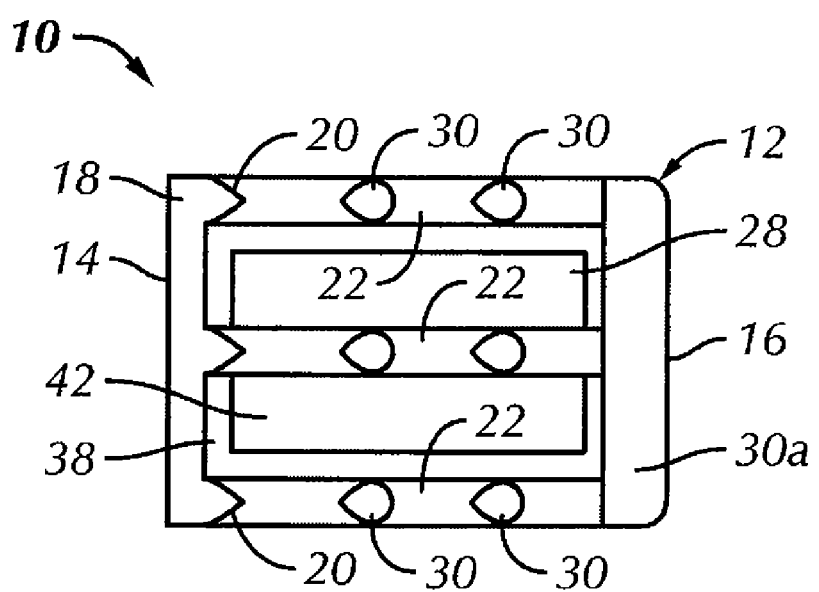
FIG. 3B is a top plan view of the cervical fixation device shown in FIG. 1B.

The frame 12 preferably tapers from the proximal end 14 toward the distal end 16 between the upper and lower arches 22, 24 such that the distance between the upper and lower arches 22, 24 decreases from the proximal end 14 toward the distal end 16. The height of the proximal end 14 as measured between the top and the bottom is greater than the height of the distal end 16 as measured between the top and the bottom to maintain lordotic angulation of the vertebral bodies above and below the cervical fixation device 10. This results in a generally trapezoidal shape when viewed from the side, as shown in FIGS. 2A and 2B.

The length of the frame 12 as measured between the proximal and distal ends 14, 16 is preferably between approximately 10 mm and 14 mm. The width of the frame 12 as measured between the lateral sides of the frame 12 is preferably between approximately 10 mm to 14 mm. The height of the cervical fixation device as measured between the upper and lower arches 22, 24 is the height necessary to fit between vertebral bodies 108 which is approximately 5 mm to 12 mm for a single level. The height could be increased if more than one level is needed to partially replace a damaged vertebral body 108.

The distal end 16 may include two or more generally spaced apart vertical members 36, identical and generally parallel to each other for supporting the distal ends of the upper and lower arches 22, 24. Preferably, each vertical member 36 connects an upper arch 22 to a corresponding lower arch 24. Though the use of a vertical member 36 is preferred, it is within the spirit and scope of the present invention that the distal end 16 have a different configuration such as a solid wall, a plurality of apertures of any geometric shape or be entirely open.

Referring to FIGS. 1B, 2B, 3B and 4, the cervical fixation device 10 may also include an insert 38. The insert 38 is comprised of a second material. The second material is preferably a radiotranslucent polymeric material such as PEEK. However, any biologically compatible polymer or other material which minimally interferes with imaging could be used. The insert 38 is positioned in the interior 32 of the frame 12 between the upper and lower arches 22, 24. The insert 38 forms a trapezoid or box-shaped structure corresponding to the shape of the interior 32. The insert 38 is generally in the form of a square in top plan view and trapezoidal or rectangular in side view. The insert 38 has an open central cavity 42, a generally open top and bottom and a generally closed proximal and distal ends. The insert 38 is disposed within at least a portion of the frame 12 and has lateral sides 40 exposed at least partially through the open lateral sides of the frame 12. The lateral sides 40 are generally flat with rounded or contoured edges on their surfaces. The lateral sides 40 extend generally parallel with respect to each other, surround the central cavity 42, and are preferably spaced apart along the outline of the shape which precisely complements the upper and lower arches 22, 24. Each lateral side 40 contains at least one but preferably two generally circular side openings 44 which extend from the central cavity 42 through the lateral sides 40 to allow for bone growth between the central cavity 42 and the intervertebral space 130. Although two generally circular openings 44 are shown, it is understood that more or less than two openings of different shapes could be used without departing from the spirit and scope of the invention.

The insert 38 is preferably separately constructed from the frame 12 and then assembled by snap-fitting or press-fitting with suitable mating detents, grooves, edges or the like. The cervical fixation device 10 could alternatively not include the insert 38 (FIG. 6). Bone could alternatively be used in place of the insert 38.

Surgical bone screws (not shown) could be inserted through additional holes (not shown) and/or the slots 26 in the flange 18 to further secure the cervical fixation device 10 between the vertebral bodies in lieu of or in combination with the sharpened edges 20. Other fastening devices or the like could also be utilized.

Figure 4:
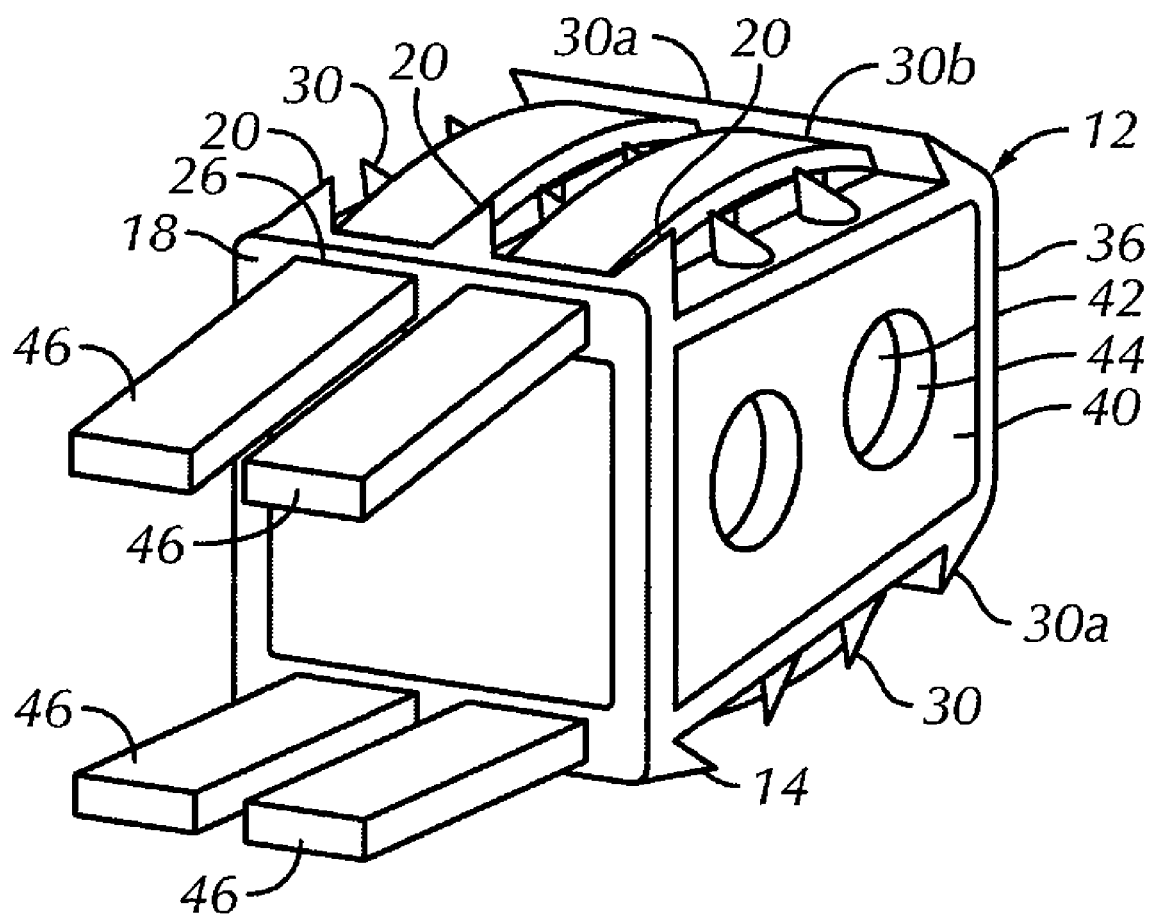
FIG. 4 is a right side rear perspective view of the cervical fixation device shown in FIG. 1B with attached protective covers.

Referring to FIG. 4, the cervical fixation device 10 may include one or more protective covers 46. The covers 46 are inserted through the slots 26 in the flange 18 and cover the gaps 28 during insertion of the cervical fixation device 10. The thickness of the covers 46 is sufficient to limit the exposure of the projections 30. When the cervical fixation device 10 is impacted, the covers 46 allow for smooth insertion by distracting the adjacent vertebrae 102. The covers 46 also prevent debris from entering the central cavity 42 or interior 32 during insertion of the cervical fixation device 10 and protect nearby anatomic structures, especially the adjacent vertebral bone surfaces, from injury by the projections 30. The protective covers 46 may curve outwardly as shown in FIG. 4 and in phantom in FIG. 2B. Additionally, the protective covers 46 may be part of or otherwise attached to the insertion tool such that the protective covers 46 are removed by or with the insertion tool.

During the insertion of the cervical fixation device 10 into the disk space using an insertion tool (not shown), two pairs of protective covers 46 are preferably used to cover the gaps 28 and to limit the exposure of the projections 30. Each of the protective covers 46 is identical and is generally in the form of a smooth surfaced stick. The protective covers 46 are of a thickness that matches the height of the projections 30, 20 and sharpened edge 30a so that preferably no sharp point or surface of the projections 30, 20 or the sharpened edges 30a protrudes beyond the smooth surface of the protective covers 46. The sharpened edges 20 may extend beyond the protective covers 46 so that they may be partially driven into the anterior margins of the adjacent vertebral bodies 108. The covers 46 extend through the slots 26 in the proximal end 14.

The insertion tool may be formed of any substantially rigid material, but preferably is formed of titanium, hardened stainless steel, or a biocompatible alloy, composite, polymeric material or the like of sufficient strength. It should be noted that the material of construction of the insertion tool could be any material without diverging from the broad scope of the present invention. The protective covers 46 are preferably made of a biocompatible polymer that is strong and somewhat flexible. However, other materials could be used, such as low density metal alloys, without departing from the spirit or scope of the invention.

During the insertion procedure, an incision is made in an anterior region of a patient proximate a small gap between a first vertebra and a second vertebra 102 of a spine of the patient. Distraction pins (not shown) are inserted into the vertebral bodies 108 above and below the disk space 130 specified for fusion. A distal end of a surgical instrument in inserted to remove disk material 128 from an intervertebral space 130 between the first and second vertebrae 102. The adjacent vertebrae 102 are then prepared for fusion, particularly proximate the anterior margins 108a to accept the cervical fixation device 10 such that the cervical fixation device 10 does not protrude beyond the anterior vertebral margins 108a. The intervertebral space 130 may then be measured such that the appropriately sized cervical fixation device 10 is selected. Once the appropriately sized cervical fixation device 10 is selected, the cervical fixation device 10 having the protective covers 46 is inserted into the intervertebral space 130 between the first and second vertebrae 102 such that the proximal end 14 is generally flush with an anterior edge of the first and second vertebrae 102. The protective covers 46 are removed to expose an interior 42 of the cervical fixation device 10 and the at least one projection 30 extending from the cervical fixation device 10. The at least one projection 20, 30 and edges 30a engage the bone to hold the cervical fixation device 10 in place. A solid bone graft or the insert 38 containing bone or non bone material is inserted into the cervical fixation device 10 to promote fusion. The insert 38 may be inserted before insertion of the frame 12.

Figure 5A:
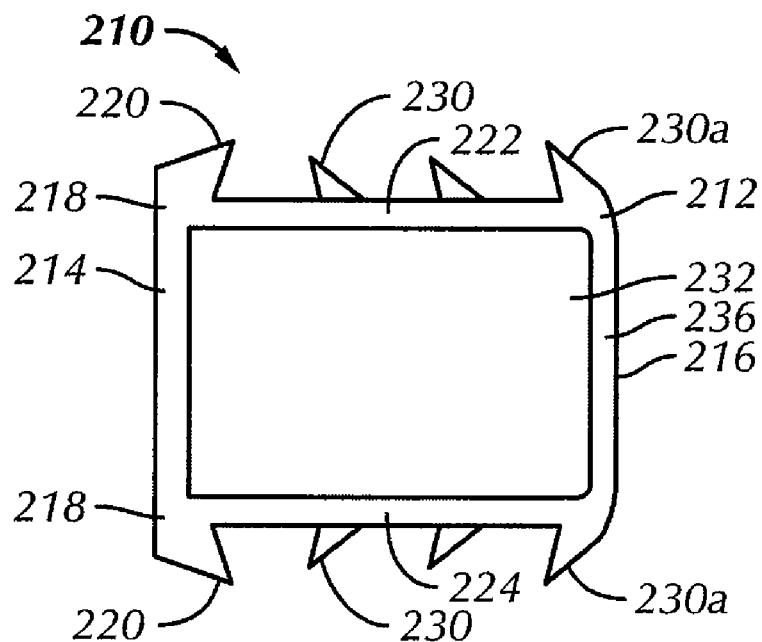
FIG. 5A is a right side elevation view of a second preferred embodiment of a cervical fixation device in accordance with the present invention.
Figure 5B:
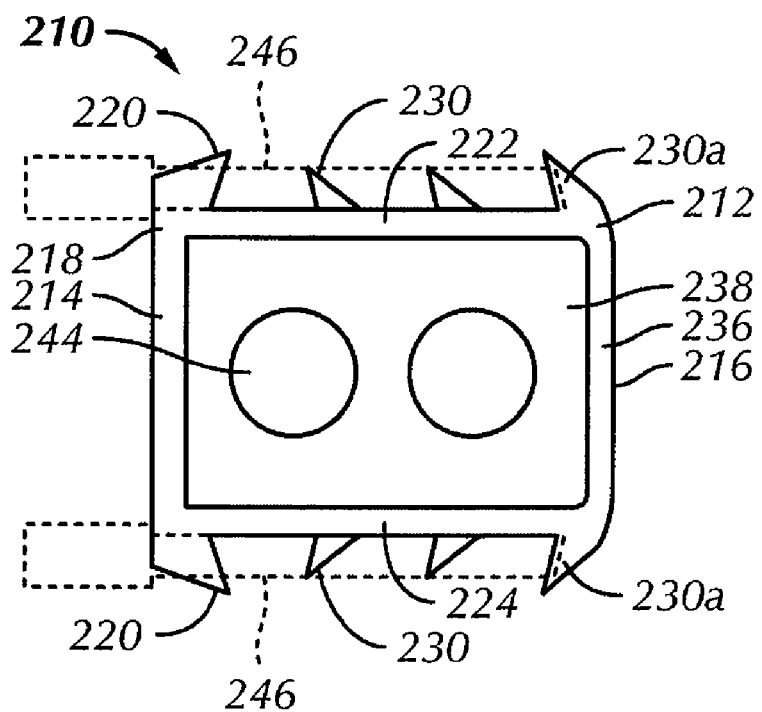
FIG. 5B is a right side elevation view of the cervical fixation device of FIG. 5A including an insert.

Referring to FIGS. 5A-5B, a second preferred embodiment of the cervical fixation device 210 includes generally parallel upper and lower arches 222, 224. The height of the proximal end 14 as measured between the top and the bottom is generally equal to the height of the distal end 16 as measured between the top and the bottom. The cervical fixation device 210 of the second preferred embodiment is nearly identical to the first embodiment of the cervical fixation device 10 except that the upper and lower arches 222, 224 form a generally rectangular shape when viewed from the side. Similar numbers indicate similar elements as discussed above for the first embodiment. A discussion of the similar features has been eliminated for convenience only and is not limiting.

It will be appreciated by those skilled in the art that changes could be made to the embodiments described above without departing from the broad inventive concept thereof. It is expected that materials science will create polymers that will allow the combination of fixation, support strength, and subsidence prevention which are embodied in the invention and thus new materials could be used in a single composition without departing from the spirit and scope of the present invention. It is understood, therefore, that this invention is not limited to the particular embodiments disclosed, but it is intended to cover modifications within the spirit and scope of the present invention as defined by the appended claims.

I claim:

1. A cervical fixation device for insertion between a pair of adjacent cervical vertebrae, the cervical fixation device comprising:

a frame comprised of a first material and having a generally rectangular proximal end and a generally rectangular distal end, a longitudinal axis of the frame extending from the proximal end to the distal end, the distal end connected to the proximal end by three upper arches and three lower arches extending generally parallel to each other, the upper and lower arches being permanently joined together by the proximal and distal ends, vertically spaced apart from each other and extending from the proximal end to the distal end, the frame having a generally hollow interior and having substantially open lateral sides and a substantially open proximal end, the three upper arches being laterally spaced apart and defining a gap between each adjacent pair of upper arches configured to promote bone growth within an intervertebral space, the three lower arches being laterally spaced-apart and defining a gap between each adjacent pair of lower arches configured to promote bone growth within the intervertebral space, the proximal end including at least one flange extending perpendicularly to the longitudinal axis above and below a remainder of the frame, the flange having at least one sharpened edge projecting toward the distal end, wherein the flange prevents the proximal end of the device from entering the intervertebral space beyond an anterior margin of the cervical vertebrae, and wherein the flange aids in fixation by engaging the vertebrae above and below the device to prevent distal migration of the device into a spinal canal, the distal end having at least one sharpened edge projecting toward the proximal end, each arch of at least one of the three upper arches and the three lower arches having at least one sharpened projection extending toward the proximal end, wherein the frame tapers from the proximal end toward the distal end between the upper and lower arches such that the vertical distance between the upper and lower arches decreases from the proximal end toward the distal end, and wherein at least one protective cover extends through a slot in the flange during insertion of the cervical fixation device, the cover having a smooth surface and being configured to curve outwardly to aid in distraction and covering the gaps between adjacent pair of arches of at least one of the three upper arches and the three lower arches, the cover having a sufficient thickness to match a height of the projections of the three arches of at least one of the three upper arches and the three lower arches such that no sharp point of the projections protrudes beyond the smooth surface of the cover to protect adjacent vertebral bone surfaces during insertion of the device.

2. The cervical fixation device of claim 1, wherein the first material is formed at least partially of a generally rigid biocompatible material selected from the group consisting of: machined bone, titanium, a nickel plated metal, an alloy, a ceramic, a polymeric material and a biologically absorbable material.

3. The cervical fixation device of claim 1, further including an insert comprised of a second material, the insert forming a box-shaped structure similar to the hollow interior of the frame, the insert disposed within at least a portion of the frame and having lateral sides exposed at least partially through the open lateral sides of the frame, the insert having a generally hollow interior.

4. The cervical fixation device of claim 3, wherein the second material is formed at least partially of a biocompatible material selected from the group consisting of: a ceramic, a polymeric material and a biologically absorbable material.

5. The cervical fixation device of claim 3, wherein the exposed lateral sides of the insert each includes at least one opening.

6. The cervical fixation device of claim 1, further comprising an interior that is generally defined by a shape of the frame.

7. The cervical fixation device of claim 6, wherein the interior houses at least one bone graft.

8. The cervical fixation device of claim 6, wherein the interior houses non-bone matter.

9. The cervical fixation device of claim 1, wherein the frame includes at least one upper protective cover that covers the gaps between adjacent pair of the upper arches during insertion of the cervical fixation device.

10. The cervical fixation device of claim 1, wherein each lower arch has at least one sharpened projection extending therefrom.

11. The cervical fixation device of claim 10, wherein the at least one sharpened projection of each lower arch extends toward the proximal end of the cervical fixation device.

12. The cervical fixation device of claim 1, wherein a length of the frame, as measured between the proximal and distal ends, is approximately equal to a width of the frame, as measured between the lateral sides.

* * * * *